United States Patent [19]

Kotun et al.

[11] Patent Number: 5,227,539
[45] Date of Patent: Jul. 13, 1993

[54] PROCESS FOR PRODUCING SALTS OF FLUORINATED ALCOHOLS

[75] Inventors: Stefan Kotun, Wharton, N.J.; Darryl Desmarteau, Clemson, S.C.; Walter Navarrini, Milan, Italy

[73] Assignee: Ausimont S.p.A., Milan, Italy

[21] Appl. No.: 786,179

[22] Filed: Oct. 31, 1991

[30] Foreign Application Priority Data

Nov. 2, 1990 [IT] Italy .................. 21964 A/90

[51] Int. Cl.$^5$ .................................. C07C 31/34
[52] U.S. Cl. ................................. 568/842; 568/846
[58] Field of Search ................ 568/841, 842, 846

[56] References Cited

U.S. PATENT DOCUMENTS 4,968,848  11/1990  Kruse et al. .................. 568/842

FOREIGN PATENT DOCUMENTS 326286   8/1989  European Pat. Off. .
168941   3/1906  Fed. Rep. of Germany .
1912405  2/1958  Fed. Rep. of Germany .
3805534  8/1989  Fed. Rep. of Germany .
102475   8/1977  Japan .

OTHER PUBLICATIONS

Soviet Patents Abstracts, SU 1567-566-A, Jun. 1991.
Journal of the American Chemical Society, vol. 111, pp. 393-395, 1989.
Chemical Abstracts, vol. 77, Abstract No. 75 253h and Chem. Lett., 1972, (6), 435-436, Sep. 1977.

*Primary Examiner*—Marianne M. Cintins
*Assistant Examiner*—Rebecca Cook
*Attorney, Agent, or Firm*—Bryan Cave

[57] ABSTRACT

Process for preparing alkali-metal or ammonium salts of fluorinated tertiary alcohols $$RxR'y(C_nF_{2n+1})kC-OM$$

wherein R and R', which may be either equal to, or different from, each other, represent a perhalocarbyl group, the halogen atoms of which are constituted by F and Cl and/or Br, a hydrogenated halocarbyl group, the halogen atoms of which are constituted by F and Cl and/or Br; n is comprised within the range of from 1 to 6; M is an alkali metal or an ammonium ion; x and/or y are 0 or 1; and k is 1, 2 or 3, with the proviso that x+y+z=3, by means of the reaction of a carbonyl compound $$R''-CO-R''',$$

in which R'' and/or R'''=R and/or R' or F, with a tri(alkyl)silane-perfluoroalkyl compound [(C$_1$-C$_4$)-alkyl]$_3$—Si—CnF$_{2n+1}$ and with a fluoride MF, in an aprotic solvent, at a temperature comprised within the range of from −45° C. to +120° C.; from said salts, the corresponding alcohols can be obtained by acidic hydrolysis. Some of the obtained products are per se novel.

27 Claims, No Drawings

PROCESS FOR PRODUCING SALTS OF FLUORINATED ALCOHOLS

The present invention relates to a process for preparing alkali-metal salts of fluorinated tertiary alcohols.

In particular, the present invention relates to a process for the direct preparation of alkali-metal salts of fluorinated tertiary alcohols, and in particular, perfluorinated or perhalogenated alcohols in which the halogen atoms are constituted by F and Cl and/or Br, by means of the reaction of the corresponding carbonylic compounds with tri(alkyl)silane-perfluoroalkyl compounds and fluorinated salts of alkali metals.

The alkali-metal salts of the tertiary alcohols, which are obtained in that way, can find use as polymerization initiator agents, for example fluoroepoxides, or as accelerator agents in the polymerization in dispersion of fluoroolefins, and so forth. From the salts, the relevant tertiary alcohols are easily obtained (by hydrolysis), which tertiary alcohols are, in their turn, products which can find interesting applications as solvents, intermediates, e.g., in the preparation of esters and peroxides, and as fumigating agents, and so forth.

As far as the present Applicant knows, no processes are described for the direct production of salts of fluorine-containing tertiary alcohols and, in particular, of fluorinated, perhalogenated alcohols. In general, multi-step processes are described, which fall outside of the scope of the present invention.

On the other hand, the addition reaction, catalysed by KF, of tri(methyl)silane-perhalobenzene onto non-halogenated carbonylic compounds (benzaldehyde) (CA-77, 75253 h, 1971), as well as the trifluoromethylation of non-fluorinated carbonylic compounds (aldehydes, ketones), catalysed by tetrabutylammonium fluoride, optionally in the presence of potassium isobutyrate (as the initiator) (J.A.C.S. 1989, 111, 393-5), are known. In the first case, diphenylmethoxysilanes of ethereal nature, and in the second case diphenylmethoxysilanes and tertiary alcohols—owing to the reaction of hydrolysis of the silyl ethers—are obtained. However, these are catalytic addition reactions (catalysed by F⁻ ion) on non-halogenated substrates, in particular non-fluorinated substrates.

Finally, a process is known for transferring perfluoroalkyl radicals to carbonylic substrates (aldehydes or ketones), also containing perfluoroalkyl groups in their molecule, by means of the reaction of perfluoroalkyl-tri(methyl)silanes with said carbonylic compounds, catalysed by fluorides of salt character (EP-A-330058, Hoechst, 1989). However, in this case too, the substrate contains substantial hydrogenated (non-halogenated) hydrocarbyl fractions, and, furthermore, the reaction product is constituted by a silyl-ether, from which the corresponding alcohols can be obtained with a second hydrolysis step. In none of these processes is it possible to directly obtain salts of fluorinated alcohols, in particular salts of perhalofluorinated tertiary alcohols.

Summing-up, the prior art teaches the obtainment of silyl-ethereal products by means of catalytic reactions, from which the possible salts of the alcohols can be theoretically only obtained by means of distinct processing steps (hydrolysis of the ethers, salification, and so on).

The present Applicant found now that salts of fluorinated alcohols, and namely, alkali-metal salts of fluorinated tertiary alcohols can be directly prepared by means of non-catalytic process which is simple, cheap, and allows high yields to be obtained.

Therefore, a purpose of the present invention is of providing alkali-metal or ammonium slats of fluorinated tertiary alcohols, by means of a direct preparation process.

Another purpose is of providing a novel, simpler method for obtaining the corresponding tertiary alcohols, by starting from said alkali-metal or ammonium salts.

These, and still other purposes, which will be clearer for those skilled in the art from the following disclosure, are achieved, according to the present invention, by a process for preparing alkali-metal salts of fluorinated tertiary alcohols of formula:

$$R_xR'_y(C_nF_{2n+1})_kC\text{—}OM \quad (I)$$

wherein

'R and R', which may be either equal to, or different from, each other, represent a perhalocarbyl group, the halogen atoms of which are constituted by F and Cl and/or Br, a hydrogenated halocarbyl group, the halogen atoms of which are constituted by F and Cl and/or Br;

n represents an integer comprised within the range of from 1 to 6, limits included, and M represents an alkali metal or the cation of an ammonium base, x and/or y represent either 0 or 1, and k is 1, 2 or 3, with the proviso that x+y+k=3, which process is characterized in that a carbonyl compound of formula (II):

$$R''\text{—}CO\text{—}R''' \quad (II)$$

in which the symbols R'' and/or R''' have the meaning as defined hereinabove for R and R' or represent F, is reacted with a tri(alkyl)silane-perfluoroalkyl compound of formula (III):

$$[(C_1\text{-}C_4)\text{-alkyl}]_3Si\text{-}C_nF_{2n+1} \quad (III)$$

wherein n has the meaning as defined hereinabove, and with an alkali-metal or ammonium fluoride MF, in an aprotic dipolar solvent, at a temperature comprised within the range of from −45° C. to +120° C.

In that way, the alkali-metal or ammonium slats of formula (I) are obtained with yields of the order of 90%.

In groups R and R', F and Cl atoms are preferably present.

From thus obtained salts of formula (I), the corresponding fluorinated tertiary alcohols can be prepared by means of conventional techniques, e.g., by hydrolysis with mineral acids, preferably with $H_2SO_4$.

More explicitly, the process according to the present invention consists in reacting a carbonylic compound of formula (II) with an alkali-metal or quaternary ammonium cation fluoride MF, and with a tri(alkyl)silane-perfluoroalkyl compound of formula (III), which releases its perfluoroalkyl group $-C_nF_{2n-1}$, transferring it to the carbonylic substrate (II). The process can be substantially carried out according to such ratios as requested by the stoichiometry of the reactions (1), (3) and (5) as set forth hereinunder, in a dipolar, aprotic, anhydrous solvent and at a temperature which can even be room temperature.

As already said, from the alkali-metal or quaternary ammonium salt (I) obtained in that way, which is a useful product, which can be sued as such in various applications, the corresponding alcohol can be obtained by means of the hydrolysis thereof, according to conventional techniques.

In the overall, the reactions implied can be schematically shown as follows.

When the substrate (II) is of ketonic type (R'', R''' = R, R'):

$$R''R'''C = O + (Alkyl)_3Si-C_nF_{2n+1} + MF \xrightarrow{\text{solvent}} \quad 1)$$
$$(II) \qquad\qquad (III)$$

$$RR'(C_nF_{2n+1})C-OM + (Alkyl)_3SiF$$
$$(I)$$

and then, if so desired:

$$(I) \xrightarrow{H^+} RR'(C_nF_{2n+1})C-OH + M^+ \quad 2)$$

in which the symbols have the above defined meaning.

If the substrate is an acyl fluoride (R''' = F, R'' = R or R'), the stoichiometry requires 2 equivalents of compound (III).

$$R''C(O)-F + 2(Alkyl)_3Si-C_nF_{2n+1} + MF \xrightarrow{\text{solvent}} \quad 3)$$
$$(II) \qquad\qquad (III)$$

$$R(C_nF_{2n+1})_2C-OM + 2(Alkyl)_3SiF \text{ and}$$

$$(I) \xrightarrow{H^+} R(C_nF_{2n+1})_2C-OH + M^+ \quad 4)$$

in which the symbols have the above defined meaning.

Finally, if the substrate is constituted by carbonyl fluoride $COF_2$ [R'' = R''' = F and x = y = 0 in formula (I)], the stoichiometry becomes:

$$COF_2 + 3(Alkyl)_3-Si-C_nF_{2n+1} + MF \xrightarrow{\text{solvent}} \quad 5)$$
$$(II) \qquad\qquad (III)$$

$$(C_nF_{2n+1})_3C-OM + 3(Alkyl)_3Si-F \text{ and}$$
$$(I)$$

$$(I) \xrightarrow{H^+} (C_nF_{2n+1})C-OH + M^+ \quad 6)$$

wherein the symbols have the meaning defined hereinabove.

In the case of some ketonic substrates (Reaction 1), it may happen that a secondary or tertiary group R or R' in the end product is replaced by a group $C_nF_{2n+1}$ deriving from compound (III).

The carbonylic compounds used as the starting compounds (II) are per se known, and can be prepared according to known techniques [see, e.g., Hynes, J. B. et al., Can. J. Chem, 45, 2278–2279 (1967)].

In them, the symbols R'' and R''', which may be equal to, or different from, each other, represent a F atom, or a perhalocarbyl group in which the halogen atoms are constituted by F and Cl and/or Br, or a hydrogenated halocarbyl group, the halogen atoms of which are constituted by F and Cl and/or Br, with all said groups containing from 1 to 10 carbon atoms, and, preferably, from 1 to 5 carbon atoms.

Suitable perhalocarbyl groups are the perhalogenated, preferably perfluorinated, either straight or branched-chain ($C_1$–$C_{10}$)-alkyl groups, ($C_3$–$C_{10}$)-cycloalkyl groups, ($C_6$–$C_{10}$)-aromatic groups. The hydrogenated halocarbyl groups, in which one or more cl, Br and F atoms may be present, can be defined in an analogous way.

Examples of carbonylic compounds of formula (II) are:

$CF_3CF_2CF_2(O)F$ (heptafluorobutyryl fluoride),
$CF_3(CF_2)_6C(O)F$ (perfluorooctanoyl fluoride),
$(CF_3)_2C=O$ (1,1,1,3,3,3-hexafluoro-2-propanone),
$CF_3-C(O)-CF_2Cl$ (1-chloro-1,1,3,3,3-pentafluoro-2propanone),
$CF_3-C(O)-CF_2H$ (1,1,1,3,3-pentafluoro-2-propanone),
$[(CF_3)_2CF]_2C=O$ (1,1,1,2,4,5,5,5-octafluoro-2,4-bis-(trifluoromethyl)-3-pentanone), $CF_3CF_2-C(O)F$ (pentafluoropropanoyl fluoride),
$COF_2$ (carbonyl fluoride), and so forth.

In an analogous way, the tri-(alkyl)-silane-perfluoroalkyl compounds of formula (III) are per se known and can be prepared according to usual techniques [see, e.g., Tetrahedron Lett. 25 (21) 2195–2198 (1984)].

In them, n is preferably comprised within the range of from 1 to 4, as in, e.g., tri(methyl)-trifluoromethylsilane.

The alkali-metal fluoride MF is constituted, e.g., by Na, Cs, Rb fluorides, and, preferably, KF.

According to an alternative route, anhydrous fluoride salts of quaternary ammonium can be used, in which the possible hydrocarbyl portion is not critic for the purposes of the process, with the proviso that such compounds are soluble enough in the aprotic solvent medium; commonly, an N-tetraalkyl-ammonium fluoride can be used, with N-tetrabutyl-ammonium being preferred.

As said hereinabove, the reaction is carried out in an inert organic, anhydrous medium, chosen among the dipolar aprotic solvents, in which the alkali-metal or ammonium fluoride is at least partially soluble. Ethers, such as diethyl ether, dioxane, tetrahydrofuran, including glymes (such as, e.g., 2-methoxyethylether), nitriles, such as benzonitrile, and mixtures thereof, have shown to be suitable solvents.

The reaction is preferably carried out in acetonitrile, which has been shown to secure higher yields.

However, together with the above solvents a cosolvent can be used in order to endow the system with suitable solvent properties for the reaction. An example of such cosolvents are crown ethers, such as 18-crown-ether-6.

As regards the temperature, the reaction is carried out by operating under such conditions as to keep the solvent in the liquid state, and favour a high concentration of the carbonylic compound.

Therefore, according to the reactants used, the solvent, etc., as said hereinabove, the temperature is maintained at values comprised within the range of from −45° C. up to approximately +120° C., and preferably is comprised within the range of from −40° C. up to +25° C.

The pressure is not an influential parameter; however, the reaction is commonly carried out under atmospheric pressure; in any case, if the particular conditions so require, pressures comprised, e.g., within the range of from 1 to approximately 10 atmospheres, can be used.

As already stated, the reactants (II), (III) and the alkali-metal or ammonium fluoride are used according to ratios which are substantially in compliance with the stoichiometry of implied reactions (1), (3) and (5), according to whether the substrate (II) is of ketonic type (1), or of acylic type (3), or is constituted by carbonyl fluoride (5).

The following molar ratios are commonly used:

Molar ratio of alkali-metal or ammonium fluoride (in short form: MF):tri(alkyl)silane-perfluoroalkyl compound (III) comprised within the range of from 0.5:1.0 to 5.0:1.0, preferably comprised within the range of from 1.0:1.0 to approximately 1.5:1.0.

Molar ratio of (III):(II) [wherein (II)=ketonic carbonylic compound) comprised within the range of from 1.0:0.2 to 1.0:5.0, and preferably comprised within the range of from 1.0:0.7 to approximately 1.0:2.0.

Molar ratio of (III):(II) [with (II)=acyl fluoride] comprised within the range of from 1.8:1.0 to 5.0:1.0, and preferably comprised within the range of from 2.0:1.0 to 2.4:1.0.

Finally, the molar ratio of (III):(II) [with (II)=COF$_2$] is comprised within the range of from 2.8:1.0 to 5.0:1.0, and is preferably comprised within the range of from 2.0:1.0 to 3.5:1.0.

The reaction times may vary within a wide range, according to the operating conditions, the starting substrate, and so forth; and normally are of from 1 to 48 hours; commonly, times comprised within the range of from 5 to about 16 hours are enough; finally, the process is preferably carried out under an inert atmosphere (argon, nitrogen, and the like).

As already said, from the alkali-metal or ammonium salts obtained according to the present invention the relevant fluorinated tertiary alcohols can be prepared, e.g., by acidic hydrolysis. Concentrated mineral acids can be used; usually, H$_2$SO$_4$ is employed. The reaction of hydrolysis is preferably carried out in the presence of stoichiometric excess of H$_2$SO$_4$, at room or lower-than-room temperature. Commonly, molar ratios of metal salt:H$_2$SO$_4$ (as 100% H$_2$SO$_4$) comprised within the range of from 1:10 to about 1:50 are used.

According to an alternative, preferred operating mode, one can directly obtain the fluorinated tertiary alcohol by performing the acidic hydrolysis in situ, without separating the metal salt, by adding to the reaction mixture, e.g., concentrated H$_2$SO$_4$ according to a molar ratio of carbonylic compound (II):H$_2$SO$_4$ (expressed as 100% H$_2$SO$_4$) comprised within the range of from 1.0:10.0 to 1.0:1:100.0, preferably comprised within the range of from 1.0:15.0 to about 1.0:50.0, substantially at room or lower-than -room temperature.

In that way, the fluorinated tertiary alcohols are obtained which correspond, e.g., to the relevant alkali-metal salts, for example:

(CF$_3$)$_3$C—OH (perfluoro-tert.butanol-propanol);
(ClCF$_2$)(CF$_3$)$_2$C—OH (1,1,1,3,3,3-hexafluoro-2-(chlorodifluoromethyl)-2-propanol);
(HCF$_2$)(CF$_3$)$_2$C—OH (1,1,13,3,3-hexafluoro-2-(difluoromethyl)-2-propanol);
[(CF$_3$)$_2$CF](CF$_3$)$_2$C—OH (1,1,1,3,4,4,4-heptafluoro-2,3-bis-(trifluoromethyl)-2-butanol;
(CF$_3$CF$_2$)(CF$_3$)$_2$C—OH (1,1,1,3,3,4,4,4-octafluoro-2-(trifluoromethyl)-2-butanol;
CF$_3$CF$_2$CF$_2$C(CF$_3$)$_2$—OH (1,1,1,3,34,4,5,5,5-decafluoro-2-(trifluoromethyl)-2-pentanol);
CF$_3$(CF$_2$)$_6$C(CF$_3$)$_2$—OH (1,1,1,3,3,4,4,5,5,6,6,7,7,8,8,9,9,9-perfluoro-2-(trifluoromethyl)-2-nonanol).

The products of formula:
(HCF$_2$)(CF$_3$)$_2$C—OM, which can be obtained by starting from CF$_3$—C(O)—CF$_2$H, and tri(methylsilane)-perfluoromethyl, together with the corresponding alcohol, are per se new and are comprised within the scope of the instant invention.

Therefore, in the process according to the present invention it is possible to directly obtained the salts (and therefrom the relevant tertiary alcohols of formula (I), having interesting applications) by a simple route, and with high yields.

Finally, the process according to the present invention is compatible, with evident economic and industrial operating advantages, with a continuous mode of operation of a facility.

The present invention is illustrated now in greater detail by referring to the following examples, which are anyway supplied for illustrative purposes, and in no way should be understood as being limitative of the purview of the invention.

In particular, in the following examples, carried out according to batch procedures, due to experimental reasons, the reactants were transferred by condensing them inside the reactor at liquid nitrogen temperature, thereby avoiding, among other, premature reactions during the transfer step and then letting the temperature to rise again to the specified operating values.

EXAMPLE 1 a) Preparation of the potassic salt of (I):(CF$_3$)$_3$C—OK 0.16 g (2.8 mmol) of KF, previously melted and ground under a N$_2$ blanketing atmosphere, was charged to a reactor, constituted by a Pyrex(TM) bulb of 100 ml of capacity, equipped with magnetic bar stirring means, inlet devices and vacuum outlet devices for the volatile materials, and with a pierceable cap for charging solvent and liquid materials to the reactor.

The reactor was then evacuated (down to a residual pressure of 10 mmH$_g$) and through the pierceable cap 4.0 ml of anhydrous acetone was charged. The reactor was then cooled down to −196° C. with liquid nitrogen.

Thereafter, 2.20 mmol of (CF$_3$)$_2$C=O and 2.19 mmol of (CH$_3$)$_3$Si—CF$_3$ were charged to the reactor, through the gas feed system, and condensed. At the end, the reactor was transferred into a bath of CFCl$_3$ at −40° C., with stirring being started up. 9 hours later, the bath was removed and stirring was continued at the temperature of 18° C., for a further 3 hours.

On a sample of the reaction mixture, the absence of (CH$_3$)$_3$Si—CF$_3$ was demonstrated. Then the solvent and the other volatile materials were removed by pumping (3 hours, 18° C.). In that way, a white solid was obtained, which was washed with a total of 40 ml of diethylether, subdivided into 4 portions, from which, combined and concentrated to dryness, a white solid was isolated (0.56 g, yield 92.8%).

NMR, IR and elemental analyses agree with the expected formula.

b) Hydrolysis of salt (I)

Concentrated sulfuric acid (3 ml, 18 M) was injected through the pierceable cap at 18° C. An exothermic reaction with effervescence occurred. After 1 hour, the volatiles were removed by pumping and were collected inside an "U"-trap kept at −196° C. The crude product was then fractionated under conditions of dynamic vacuum, through traps kept cooled at −50° C., −85° C.

and −196° C. The trap at −85° C. was found to contain 2.00 mmol of (CF$_3$)$_3$C—OH, with a yield of 90.9% relatively to the carbonylic compound used as the starting reactant.

The identity of the product, perfluoro-tert.-butanol, was confirmed on the basis of IR, $^{19}$F/$^1$H-NMR and mass spectra. The IR spectrum was identical to the spectrum of an authentic sample.

EXAMPLE 2 a) Preparation of the potassic salt of 1,1,1,3,3,3-hexafluoro-2-(chlorodifluoromethyl)-2-propanol (I) (ClCF$_2$)—(CF$_3$)$_2$C—OK.

0.14 g (2.4 mmol) of KF was charged to the reactor, using the same equipment and according to the same operating modalities as of Example 1(a), then through the pierceable cap 4.0 ml of anhydrous acetonitrile was injected, and air was evacuated, while the reactor was being cooled down to −196° C.

Thereafter, 2.20 mmol of chloropentafluoroacetone:

CF$_3$—C(O)—CF$_2$Cl, purified by vacuum distillation, and 2.19 mmol of (CH$_3$)$_3$Si—CF$_3$ were added, and were condensed at −196° C. The reactor was then placed inside a CFCl$_3$ bath kept at the temperature of −40° C.; the reaction mixture was stirred for 15.5 hours while being allowed to warm up to 19° C., and stirring was continued for a further 2.5 hours.

By operating as in Example 1(a), a solid material of yellow-whitish colour was obtained (0.58 g, yield 91%).

NMR, IR and elemental analyses are in compliance with the expected formula.

b) Hydrolysis of salt (I)

By operating as disclosed in Example 1(b), the salt obtained from 2(a) was hydrolysed, by using 4.0 ml of concentrated H$_2$SO$_4$, and the crude product of hydrolysis was collected inside an "U"-shaped trap at −196° C., by pumping at 19° C., over a period of 50 minutes, then said product was fractionated by being collected inside traps kept cooled at −35° C., −70° C. and −196° C. From the trap at −70° C., 1.94 mmol of tertiary alcohol ClCF$_2$(CF$_3$)$_2$C—OH was collected, with a yield of 88.6% relatively to the carbonylic compound used as starting reactant. The identity of the tertiary alcohol produced was confirmed by IR, $^{19}$F/$^1$H-NMR and mass spectrographic analyses.

EXAMPLE 3 a) Preparation of the potassic salt of 1,1,1,3,3,3,-hexafluoro-2-(difluoromethyl)-2-propanol (I): HCF$_2$(CF$_3$)$_2$C—OK By operating as in above Examples 1 and 2, 0.30 g of KF (5.2 mmol) was charged to the reactor, and 8.0 ml of anhydrous acetonitrile was added. After removing air, to the reactor, at −196° C., 2.40 mmol of pentafluoroacetone

CF$_3$C(O)—CF$_2$H and 2.40 mmol of (CH$_3$)$_3$—Si—CF$_3$ were then added.

The reaction mixture was then heated up to −40° C. inside the bath of CFCl$_3$, with stirring. After 15.5 hours of reaction, with the bath being slowly heated, the latter was removed and stirring was continued at 19° C., for a further 45 minutes; a dark brown coloured reaction mixture was obtained. By operating as in Example 1(a), after removing the volatiles by pumping at 19° C. for 6.5 hours, a sticky material (0.282 g, yield 46%) with a brown colour was obtained.

b) Hydrolysis of salt (I)

By operating as in Example 1(b), to the salt, obtained from 3(a), 4.0 ml of concentrated H$_2$SO$_4$ was added; the crude product of hydrolysis was collected, by submitting said product to pumping at 19° C. for a 50 minutes time, inside an "U"-shaped trap, kept cooled at −196° C. The product was then fractionated by distillation into traps kept cooled at −60° C., −80° C. and −196° C. In that way, from the trap kept at −80° C., 0.96 mmol of the tertiary alcohol

HCF$_2$C(CF$_3$)$_2$—OH corresponding to the title salt, was collected, with a yield of 40% relatively to the carbonylic compound.

This alcohol is a per se novel compound, which has been characterized on the basis of the following IR, $^{19}$F/$^1$H-NMH and mass spectra:

IR (3 torr): 3617 (νO—H, sharp, m), 3002 (νC—H, w), 1402 (m), 1374 (sh, m), 1362 (m), 1279 (sh, vs) 1254 (sh, vs), 1243 (vs), 1185 (s), 1140 (s), 1124 (sh, m), 1098 (w), 1059 (m), 989 (sh, m), 964 (s), 957 (sh, m), 856 (vw), 815 (w), 772 (vw), 741 (m), 727 (sh, m), 674 (w), 668 (sh, w), 631 (vw), 574 (w), 523 (m) cm$^{-1}$; NMR H$^A$CF$_2$$^B$(CF$_3$$^C$)$_2$C—OH$^D$ (CDCl$_3$, 20° C.) $^{19}$F B −132.7 (2F, d-sept), C −74.7 ppm (6F, t-d); $^1$H A 6.09 (1H, t-sept), D 3.41 ppm (1H, br s); J$_{AB}$=52.7, J$_{AC}$=0.9, J$_{BC}$=9.2, J$_{AD}$=J$_{BD}$=J$_{CD}$=0 Hz; major m/z [EI]: 179 (M—HF—F)$^+$, 167 (M—CF$_2$H)$^+$, 148 (M—LF-$_2$H—F)$^+$, 129 (CF$_2$COHCF)$^+$, 128 (CF$_3$COCF)$^+$, 97 (CF$_3$CO)$^+$, 69 (CF$_3$)$^+$, 60 CFCOH)$^+$, 51 (CF$_2$H)$^+$, 50 (CF$_2$)$^+$; major m/z [CI]; 219 (MN)$^+$, 199 (MH—HF)$^+$, 179 (MF—2HF)$^+$, 149 (M—CF$_3$)$^+$, 129 (M—HF—CF$_3$)$^+$, wherein: sh=sharp w=weak; m=medium; vs=very strong; s=strong; vw=very weak; d-sept-=septet doublet; t-sept=septet triplet; br=broad; t-d=doublet triplet.

EXAMPLE 4 a) Preparation of the potassic salt of 1,1,1,3,4,4,4-heptafluoro-2,3-bis(trifluoromethyl)-butanol (I) [(CF$_3$)$_2$CF](CF$_3$)$_2$C—OK.

By operating as in the above examples, 262.2 mg (0.9925 mmol) of 18-crown-ether-6, as cosolvent to increase the KF solvent power, was added to the reactor and to it 0.20 g (3.4 mmol) of KF was added, followed, after evacuating the reactor down to 10 mm$_{Hg}$, by 5.0 ml of anhydrous diethyl ether.

Subsequently by cooling with liquid nitrogen, 3.0 mmol of bis(perfluoroisopropyl)ketone

[(CF$_3$)$_2$CF]$_2$C=O and 3.30 mmol of $$(CH_3)_3Si-CF_3$$

were charged and condensed.

The reactor was then brought to the temperature of −10° C. in a bath of CFCl$_3$, during 0.5 hours, with stirring, and stirring was continued for a further 11.5 hours at 20° C. By operating as in Example 1(a), and continuing to remove the volatiles by pumping at 20° C. for a 1.5 hours time, a solid material of yellow-white colour was obtained (0.148 g, yield 13.2%), which, on the basis of the usual $^{19}$F-NMR, mass, etc., analyses, was recognized to be the product of the title.

b) Hydrolysis of salt (I)

By operating as in the preceding examples, to the salt obtained from 4(a), H$_2$SO$_4$ (5.0 ml) at 20° C. was added. The volatiles were then collected inside a trap kept cooled at −196° C. by a 2-hour pumping at 20° C.

The following fractionation inside traps kept cooled at −40° C., −60° C. and −196° C. allowed 0.35 mmol of tertiary alcohol:

$$[(CF_3)_2CF](CF_3)_2C-OH$$

to be collected inside the trap at −60° C., with a yield of 11.6%, relatively to the ketone used as starting compound.

The identity of the tertiary alcohol produced was confirmed by IR, $^{19}$F/$^1$H—NMR and mass spectrographic analyses.

EXAMPLE 5 a) Preparation of the potasssic salt of 1,1,1,3,3,4,4,4-octafluoro-2-(trifluoromethyl)-2-butanol (I) (CF$_3$CF$_2$)(CF$_3$)$_2$C—OK By operating as in the above examples, 0.26 g of KF (4.5 mmol) was charged to the reactor, and then 4.0 ml of anhydrous acetonitrile was injected through the pierceable cap; the whole was then cooled down to −196° C. with the residual air being evacuated; then, 2.0 mmol of pentafluoropropionyl fluoride $$CF_3CF_2-C(O)F$$

and 4.30 mmol of $$(CH_3)_3Si-CF_3$$

were charged. After keeping the reaction vessel inside a CFCl$_3$ bath at −40° C., with stirring, for 9.5 hours, the bath was removed and stirring was continued for a further 7 hours at 20° C.

Still by operating according to Example 1(a), the subsequent removal of the solvent and of the volatile matter by pumping at 20° C. for a 7.25 hour time gave a residue constituted by a pale brown powder (0.584 g, yield 90%), which was recognized to be the product of the title.

The halt has been characterized on the basis of $^{19}$F—NMR analysis, which gave the following results: CF$_3^A$CF$_2$ $^B$C(CF$_3$)$_2$$^C$OK (d$_6$-acetone, 20° C.) $^{19}$F δA −78.5 (3F, sept), B −118.9 (2F, sept), C −74.8 (6F, br s); J$_{AC}$=5.4, J$_{BC}$=11.0 Hz.

b) Hydrolysis of salt (I)

By operating as disclosed in the preceding examples, to the salt (I) obtained from 5(a), 5.0 ml of concentrated H$_2$SO$_4$ at 20° C. was added. The crude hydrolysis product was then collected inside an "U"-shaped trap kep cooled at −196° C., by pumping at 20° C. for 2.5 hours.

The subsequent fractionation inside traps kept cooled at −45° C., −85° C. and −196° C. supplied 1.70 mmol of the tertiary alcohol with formula $$CF_3CF_2(CF_3)_2C-OH$$

in the trap at −85° C., with a yield of 85%, as computed relatively to the acylic compound used as starting reactant.

The identity of the tertiary alcohol produced was confirmed by IR, $^{19}$F/$^1$H—NMR and mass spectrographic analyses. The resulting spectra were identical to those obtained from a sample of known composition.

EXAMPLE 6 a) Preparation of the salt (I): (CF$_3$)$_3$C—OK. (Example 1)

By operating as in the above examples, 7.6 mmol of KF was charged to the reactor and then 4.0 ml of anhydrous acetonitrile was added under vacuum, with the mixture being cooled down to −196 C.

Then 6.7 mmol of $$(CF_3)_3Si-CF_3$$

and 2.1 mmol of COF$_2$ were added and the mixture was dipped in a bath of CFCl$_3$ at −40° C. with stirring. After 18 hours, during which the temperature increased up to 22° C., operating as in Example 1(a), a solid residue (0.455 g, yield 79%) was obtained.

The NMR, as well as the other, analyses confirm the expected formula.

b) Hydrolysis of salt (I)

By operating as in the preceding examples, to the salt (I) obtained from 6(a), 4 ml of concentrated H$_2$SO$_4$ (98%) was added under vacuum at 0° C. After 15 minutes, the volatile materials were removed by pumping at 22° C. during 45 minutes.

The tertiary alcohol with formula:

$$(CF_3)_3C-OH$$

obtained was collected in a trap at −100° C. after passage through a trap at −46° C. (0.378 g, yield 76%).

The spectroscopic properties resulted to be identical to those of a known sample.

EXAMPLE 7 a) Preparation of the potassic salt of 1,1,1,3,3,4,4,5,5,5-decafluoro-2-(trifluoromethyl)-2-pentanol (I) CF$_3$CF$_2$CF$_2$C(CF$_3$)$_2$—OK By operating as disclosed in the preceding examples, 6.0 mmol (0.35 g) of KF was charged to the reactor, and then 4.0 ml of anhydrous acetonitrile was added, with the reaction mixture being cooled down to −196° C.

Then, 4.69 mmol of $$(CH_3)_3Si-CF_3$$

and 2.0 mmol of $$CF_3CF_2CF_2C(O)F$$

were added, and the mixture was placed in an ethanol bath at −25° C., with stirring. After 15 hours, during which the temperature of the reaction mixture increased up to 20° C., operating as in Example 1(a), a brown-coloured solid residue was obtained (0.55 g, yield 73.4% computed relatively to the starting fluorinated compound), which was recognized to be the product of the title.

The salt was characterized on the basis of $^{19}$F-NMR analyses. $CF_3{}^ACF_2{}^BCF_2C^C(CF_3)_2{}^DOK$ (d$_6$-acetone, 20° C.) $^{19}F$ δ A −−80.0 (3F, t), B −123.3 (2F, m), C −115.4 (2F, m), D −74.4 (6F, br, t); $J_A = 11.7$ Hz.

b) The corresponding alcohol is obtained by hydrolysis, by operating according to Example 1

EXAMPLE 8 a) Preparation of the potassic salt of 1,1,1,3,3,4,4,5,5,6,6,7,7,8,8,9,9,9-perfluoro-2(trifluoromethyl)-2nonanol (I): $CF_3(CF_2)_6C(CF_3)_2$-OK By operating as disclosed in the preceding examples, 9.1 mmol (0.53 g) of KF was charged to the reactor, and then 6.0 ml of anhydrous acetone was added, with the reaction mixture being cooled down to −196° C.

Thereafter, 7.34 mmol of (CH$_3$)$_3$Si—CF$_3$ and 3.17 mmol of

CF$_3$(CF$_2$)$_6$C(O)F (1.32 g) were added, and the mixture was placed in an ethanol bath at −25° C., with stirring. Stirring was continued for 16 hours, during which the temperature increased up to 20° C. By operating as in Example 1(a), a crown solid residue was obtained (0.19 g, yield 10.4%, computed relatively to the fluorinated chemical used as starting compound), which was recognized to be the product of the title.

The salt was characterized on the basis of $^{19}$F-NMR analysis:

$CF_3{}^ACF_2{}^BCF_2{}^CCF_2{}^DCF_2{}^ECF_2{}^FCF_2{}^GC(CF_3)\text{-}{}^H{}_2OK$ (d$_6$-acetone, 20° C.) $^{19}F$ δ A −80.6 (3F, t, t), B −125.7 (2F, m), C −122.2 (2F, br, s), D −121.3 (2F, br, s), E −120.5 (2F, br, s), F −118.8 (2F, br, s), G −114.4 (2F, br, s), H −73.8 (6F, br, s).

b) The corresponding alcohol is obtained by hydrolysis by operating according to Example 1

We claim:

1. A process for preparing alkali-metal or ammonium salts of fluorinated tertiary alcohols having the formula (I):

$R_xR'_y(C_nF_{2n+1})_kC\text{—}OM$ (I)

wherein
R and R', may be the same or different from each other and are a perhalocarbyl group, the halogen atoms of which are F, Cl and/or Br; or a hydrogenated halocarbyl group, the halogen atoms of which are F, Cl and/or Br;
n is an integer of from 1 to 6, inclusive;
M is an alkali metal or the cation of an ammonium base;
x and/or y are 0 or 1; k is 1, 2 or 3; and x+y+k=3;

wherein a carbonyl compound having formula (II):

R″—CO—R‴ (II)

wherein R″ and/or R‴ have the meanings defined above for R and/or R' and may also be F; is reacted with a tri(alkyl)silane-perfluoroalkyl compound having formula (III):

$((C_1\text{-}C_4)\text{-alkyl})_3\text{—Si—}C_nF_{2n+1}$ (III)

and with an alkali-metal or ammonium fluoride MF, wherein n and M have the meanings defined above, in an aprotic dipolar solvent at a temperature within the range of from −45° C. to +120° C., and wherein the molar ratio of MF:(III) is from 0.5:1.0 to 5.0:1.0.

2. Process according to claim 1, in which in the carbonylic compound (II) R″ and R‴ represent a perhalocarbyl group containing from 1 to 10 carbon atoms or a hydrogenated halocarbyl group containing from 1 to 10 carbon atoms.

3. Process according to claim 2, in which R″ and R‴ contain from 1 to 5 carbon atoms.

4. Process according to claim 1, in which in the carbonylic compound (II), R″ and R‴ independently represent a perhalogenated (C$_1$-C$_{10}$)-alkyl group, a perhalogenated (C$_3$-C$_{10}$)-cycloalkyl group, a perhalogenated Aromatic C$_6$-C$_{10}$ group or a corresponding hydrogenated halocarbyl group, containing F and Cl atoms.

5. Process according to claim 1, in which in the tri(alkyl)silane-perfluoroalkyl compound of formula (III), n is an integer of from 1 to 4.

6. Process according to claim 1, in which the carbonylic compound used as the starting compound (II) is selected from the group consisting of 1,1,1,3,3,3-hexafluoro-2-propanone, 1-chloro-1,1,3,3,3-pentafluoro-2-propanone, 1,1,1,3,3-pentafluoro-2-propanone, 1,1,1,2,4,5,5,5,-octafluoro-2,4-bis-(trifluoromethyl)-3-pentanone, pentafluoro-propanoyl fluoride, carbonyl fluoride, heptafluoro butyryl fluoride and perfluorooctanoyl fluoride.

7. Process according to claim 1, in which the tri(alkyl)silane-perfluoroalkyl (III) is trimethylsilane-trifluoromethyl.

8. Process according to claim 1, in which the alkali-metal fluoride or ammonium fluoride is selected from the group consisting of Na, Cs, Rb fluorides and N-tetraalkyl-ammonium fluorides.

9. Process according to claim 1, in which potassium fluoride is used.

10. Process according to claim 1, in which the solvent medium is selected from the group consisting of ethers and nitriles, and their mixtures.

11. Process according to claim 10, in which the solvent medium is selected from the group consisting of dioxane, tetrahydrofuran, the glymes, benzonitrile and mixtures thereof.

12. Process according to claim 1, in which the solvent is acetonitrile.

13. Process according to claim 1, in which a cosolvent is used.

14. Process according to claim 1, in which the reaction temperature is within the range of from −40° C. to +25° C.

15. Process according to claim 1, which is conducted under a reaction pressure within the range of from room pressure up to approximately 10 atmospheres.

16. Process according to claim 1, in which the molar ratio of (III):Ketonic (II) is within the range of from 1.0:0.2 to 1.0:5.0.

17. Process according to claim 1, in which the ratio of (III):acylic (II) is within the range of from 1.8:1.0 to 5.0:1.0.

18. Process according to claim 1, in which the ratio of (III):$COF_2$ is within the range of from 2.8:1.0 to 5.0:1.0.

19. Process according to claim 1, in which the molar ratio of MF:(III) is within the range of from 1.0:1.0 to 1.5:1.0.

20. Process according to claim 16, in which the ratio of (II):ketonic (II) is within the range of from 1.0:0.7 to 1.0:2.0.

21. Process according to claim 17, in which the ratio of (III):acylic (II) is within the range of from 2.0:1.0 to 2.4:1.0.

22. Process according to claim 18, in which the ratio of (III):$COF_2$ is within the range of from 3.0:1.0 to 3.5:1.0.

23. Process according to claim 1, wherein the alkali-—metal salt of formula I is further subjected to acidic hydrolysis in order to obtain the corresponding tertiary alcohol.

24. Process according to claim 23, in which the hydrolysis is carried out with an excess of a mineral acid.

25. Process according to claim 24, in which the mineral acid is $H_2SO_4$ in a molar ratio of from 10:1 to 50:1.

26. Process according to claim 1, wherein the compound (I) is further transformed in situ into the corresponding tertiary alcohol, by means of the hydrolysis with $H_2SO_4$ according to a molar ratio of carbonyl compound (II):$H_2SO_4$ within the range of from 1.0:10.0 to 1.0:100.0.

27. Process according to claim 26, in which the molar ratio of (II):$H_2SO_4$ is within the range of from 1.0:15.0 to 1.0:50.0.

* * * * *